(12) United States Patent
Dreyfuss

(10) Patent No.: US 10,524,776 B2
(45) Date of Patent: Jan. 7, 2020

(54) SOFT SUTURE ANCHOR ASSEMBLY WITH BARBED SUTURE AND ATTACHED TISSUE FIXATION DISK

(71) Applicant: Arthrex, Inc., Naples, FL (US)

(72) Inventor: Peter J. Dreyfuss, Naples, FL (US)

(73) Assignee: Arthrex, Inc., Naples, FL (US)

( * ) Notice: Subject to any disclaimer, the term of this patent is extended or adjusted under 35 U.S.C. 154(b) by 435 days.

(21) Appl. No.: 15/345,952

(22) Filed: Nov. 8, 2016

(65) Prior Publication Data

US 2018/0125472 A1 May 10, 2018

(51) Int. Cl.
*A61B 17/04* (2006.01)

(52) U.S. Cl.
CPC .. *A61B 17/0401* (2013.01); *A61B 2017/0404* (2013.01); *A61B 2017/0409* (2013.01); *A61B 2017/0412* (2013.01); *A61B 2017/0462* (2013.01); *A61B 2017/0464* (2013.01)

(58) Field of Classification Search
CPC ........ A61B 17/0401; A61B 2017/0404; A61B 2017/0409; A61B 2017/0414; A61B 2017/042; A61B 2017/0458; A61B 2017/0459; A61B 2017/0461; A61B 2017/0462; A61B 2017/0464; A61B 2017/0496; A61B 2017/06176; A61F 2/0811; A61F 2002/0817; A61F 2002/0847; A61F 2002/0852; A61F 2002/0858; A61F 2002/0876; A61F 2002/0882; A61F 2002/0888
See application file for complete search history.

(56) References Cited

U.S. PATENT DOCUMENTS

| | | | | |
|---|---|---|---|---|
| 5,370,661 A | * | 12/1994 | Branch | A61B 17/0401 24/16 R |
| 5,372,146 A | * | 12/1994 | Branch | A61B 17/0401 128/898 |
| 5,520,691 A | * | 5/1996 | Branch | A61B 17/0401 24/16 PB |
| 5,645,568 A | * | 7/1997 | Chervitz | A61B 17/06166 606/228 |
| 5,725,556 A | * | 3/1998 | Moser | A61B 17/0487 128/898 |
| 5,814,056 A | * | 9/1998 | Prosst | A61B 17/0487 24/16 PB |
| 6,027,523 A | | 2/2000 | Schmieding | |
| 6,485,504 B1 | * | 11/2002 | Johnson | A61B 17/0401 606/216 |

(Continued)

FOREIGN PATENT DOCUMENTS

EP 2 774 545 A2 9/2014
WO WO 2014/031578 A1 2/2014

*Primary Examiner* — Ryan J. Severson
(74) *Attorney, Agent, or Firm* — Blank Rome LLP

(57) ABSTRACT

A suture anchor assembly and a method of tissue repair using the assembly. The assembly includes a soft suture anchor formed of a flexible tubular sheath with opposing open ends which receives a suture strand from a suture construct. The suture strand has a tensioning free end and an opposite tissue-fixation end. A tissue-fixation device, such as a disk, is coupled to the tissue-fixation end of the suture strand. The suture strand has uni-directional barbs which allow one-way tensioning, to provide secure fixation of soft tissue to bone as the strand is pulled through the sheath of the soft anchor.

11 Claims, 1 Drawing Sheet

(56) References Cited

U.S. PATENT DOCUMENTS

| | | | |
|---|---|---|---|
| 6,620,185 B1* | 9/2003 | Harvie | A61B 17/0401 606/215 |
| 7,144,414 B2* | 12/2006 | Harvie | A61B 17/00491 606/232 |
| 7,144,415 B2* | 12/2006 | Del Rio | A61B 17/0401 606/232 |
| 7,410,460 B2 | 8/2008 | Benderev | |
| 7,442,202 B2 | 10/2008 | Dreyfuss | |
| 7,572,275 B2* | 8/2009 | Fallin | A61B 17/0401 606/232 |
| 7,582,105 B2* | 9/2009 | Kolster | A61B 17/06 606/228 |
| 7,785,347 B2* | 8/2010 | Harvie | A61B 17/00491 606/232 |
| 7,959,650 B2* | 6/2011 | Kaiser | A61B 17/0401 606/232 |
| 8,088,130 B2* | 1/2012 | Kaiser | A61B 17/0401 606/139 |
| 8,118,836 B2* | 2/2012 | Denham | A61B 17/0401 606/232 |
| 8,231,654 B2* | 7/2012 | Kaiser | A61B 17/0401 606/232 |
| 8,414,612 B2 | 4/2013 | Kirsch et al. | |
| 8,562,647 B2* | 10/2013 | Kaiser | A61B 17/0401 606/232 |
| 8,608,777 B2* | 12/2013 | Kaiser | A61B 17/0401 606/232 |
| 8,652,172 B2* | 2/2014 | Denham | A61B 17/0401 606/228 |
| 8,663,277 B2 | 3/2014 | Collier et al. | |
| 8,721,664 B2 | 5/2014 | Ruff et al. | |
| 8,747,438 B2* | 6/2014 | Longo | A61B 17/0401 606/228 |
| 8,795,334 B2 | 8/2014 | Astorino et al. | |
| 8,814,904 B2* | 8/2014 | Bennett | A61B 17/0401 606/232 |
| 8,932,327 B2 | 1/2015 | Kosa et al. | |
| 8,979,895 B2* | 3/2015 | Miller | A61B 17/0401 606/139 |
| 8,986,346 B2* | 3/2015 | Dreyfuss | A61B 17/0401 606/232 |
| 9,011,487 B2* | 4/2015 | Lindh, Sr. | A61B 17/0401 606/228 |
| 9,271,706 B2* | 3/2016 | Stopek | A61B 17/0057 |
| 9,307,979 B1* | 4/2016 | Bennett | A61B 17/06166 |
| 9,345,567 B2* | 5/2016 | Sengun | A61B 17/0401 |
| 9,357,992 B2 | 6/2016 | Stone et al. | |
| 9,463,011 B2 | 10/2016 | Dreyfuss et al. | |
| 9,480,473 B2* | 11/2016 | Kim | A61B 17/0487 |
| 9,532,777 B2* | 1/2017 | Kaiser | A61B 17/0401 |
| 9,597,068 B2* | 3/2017 | Sengun | A61B 17/0401 |
| 9,700,305 B2* | 7/2017 | Bennett | A61F 2/0811 |
| 9,757,122 B2* | 9/2017 | Bennett | A61F 2/0811 |
| 9,833,234 B2* | 12/2017 | Broom | A61L 31/14 |
| 9,855,033 B2* | 1/2018 | Bennett | A61B 17/8888 |
| 9,861,351 B2* | 1/2018 | Kaiser | A61B 17/0401 |
| 9,924,937 B2* | 3/2018 | Kim | A61B 17/0487 |
| 9,962,150 B2* | 5/2018 | Rodriguez | A61B 17/0401 |
| 10,004,489 B2* | 6/2018 | Kaiser | A61B 17/0401 |
| 10,039,543 B2* | 8/2018 | Durando | A61B 17/0401 |
| 10,058,320 B2* | 8/2018 | Oren | A61B 17/0401 |
| 2003/0078585 A1* | 4/2003 | Johnson | A61B 17/0401 606/303 |
| 2003/0149447 A1 | 8/2003 | Morency et al. | |
| 2004/0049194 A1* | 3/2004 | Harvie | A61B 17/0401 606/232 |
| 2005/0267531 A1 | 12/2005 | Ruff et al. | |
| 2006/0122608 A1* | 6/2006 | Fallin | A61B 17/0401 606/232 |
| 2007/0038249 A1* | 2/2007 | Kolster | A61B 17/06 606/228 |
| 2008/0312689 A1* | 12/2008 | Denham | A61B 17/0401 606/232 |
| 2009/0082805 A1* | 3/2009 | Kaiser | A61B 17/0401 606/228 |
| 2009/0182375 A1* | 7/2009 | Isse | A61B 17/06 606/223 |
| 2009/0312776 A1* | 12/2009 | Kaiser | A61B 17/0401 606/148 |
| 2010/0036395 A1* | 2/2010 | Miller | A61B 17/0401 606/139 |
| 2010/0087854 A1* | 4/2010 | Stopek | A61B 17/0057 606/215 |
| 2010/0160963 A1* | 6/2010 | Fallin | A61B 17/0401 606/232 |
| 2010/0298871 A1 | 11/2010 | Ruff et al. | |
| 2011/0054522 A1* | 3/2011 | Lindh, Sr. | A61B 17/0401 606/228 |
| 2011/0213416 A1* | 9/2011 | Kaiser | A61B 17/0401 606/232 |
| 2012/0041485 A1* | 2/2012 | Kaiser | A61B 17/0401 606/232 |
| 2012/0290003 A1* | 11/2012 | Dreyfuss | A61B 17/0401 606/232 |
| 2013/0296934 A1* | 11/2013 | Sengun | A61B 17/0401 606/232 |
| 2014/0081325 A1* | 3/2014 | Sengun | A61B 17/0401 606/232 |
| 2014/0121700 A1 | 5/2014 | Dreyfuss et al. | |
| 2014/0194927 A1* | 7/2014 | Kaiser | A61B 17/0401 606/232 |
| 2014/0249577 A1* | 9/2014 | Pilgeram | A61B 17/0485 606/228 |
| 2014/0316460 A1 | 10/2014 | Graul et al. | |
| 2014/0364862 A1* | 12/2014 | Bennett | A61F 2/0811 606/104 |
| 2014/0364904 A1* | 12/2014 | Kim | A61B 17/0487 606/228 |
| 2015/0051642 A1* | 2/2015 | Broom | A61L 31/14 606/228 |
| 2015/0173739 A1* | 6/2015 | Rodriguez | A61B 17/0401 606/232 |
| 2015/0173754 A1 | 6/2015 | Norton et al. | |
| 2015/0257750 A1* | 9/2015 | Kaiser | A61B 17/0401 606/232 |
| 2015/0351740 A1* | 12/2015 | Bennett | A61F 2/0811 606/232 |
| 2015/0351759 A1* | 12/2015 | Bennett | A61F 2/0811 606/228 |
| 2016/0051246 A1 | 2/2016 | Durando | |
| 2016/0135797 A1* | 5/2016 | Stopek | A61B 17/0057 606/215 |
| 2016/0174963 A1* | 6/2016 | Oren | A61B 17/0401 606/232 |
| 2016/0242760 A1* | 8/2016 | Kaiser | A61B 17/0401 |
| 2016/0310130 A1* | 10/2016 | Pilgeram | A61B 17/0485 |
| 2017/0035411 A1* | 2/2017 | Kaiser | A61B 17/0401 |
| 2017/0042531 A1* | 2/2017 | Kim | A61B 17/0487 |
| 2017/0143329 A1* | 5/2017 | Sengun | A61B 17/0401 |
| 2017/0325802 A1* | 11/2017 | Bennett | A61B 17/06166 |
| 2018/0116661 A1* | 5/2018 | Bennett | A61B 17/8888 |
| 2018/0125472 A1* | 5/2018 | Dreyfuss | A61B 17/0401 |
| 2018/0125476 A1* | 5/2018 | Kaiser | A61B 17/0401 |
| 2018/0153538 A1* | 6/2018 | Kaiser | A61B 17/0401 |
| 2018/0168567 A1* | 6/2018 | Kim | A61B 17/0487 |
| 2018/0228484 A1* | 8/2018 | Rodriguez | A61B 17/0401 |

* cited by examiner

SOFT SUTURE ANCHOR ASSEMBLY WITH BARBED SUTURE AND ATTACHED TISSUE FIXATION DISK

FIELD OF THE INVENTION

The present invention relates to a suture anchor assembly used for attachment of tissue to bone, and more particularly to a soft suture anchor assembly with a barbed suture and an attached tissue fixation disk.

BACKGROUND OF THE INVENTION

Various types of suture anchors have been developed for securing soft tissue to bone. U.S. Pat. No. 6,027,523 to Schmieding and U.S. Pat. No. 7,442,202 to Dreyfuss, both of which are herein incorporated by reference, disclose a tissue repair method using a rigid anchor structure with a driving end for creating a hole in bone and an opposing disk for capturing the soft tissue. A need exists for a simplified anchor solution used in soft tissue repair that sufficiently fixes the soft tissue to bone and locks the same in place.

SUMMARY OF THE INVENTION

Accordingly, the present invention provides a suture anchor assembly that comprises a soft suture anchor and a suture construct for fixation of soft tissue to bone. The soft suture anchor is formed of a flexible tubular sheath with opposing open ends, and receives a suture strand that forms parts of a suture construct. The suture strand has a tensioning free end and an opposite tissue-fixation end. A tissue-fixation structure, such as a mesh disk or button, is attached to the tissue-fixation end of the suture strand. A locking structure, such as a plurality of uni-directional barbs, is disposed on at least a portion of the suture strand between the tensioning free and tissue-fixation ends thereof.

The present invention may also provide a method of tissue repair, comprising the steps of loading a soft anchor with a suture construct including a suture strand passing through a tubular sheath of the soft anchor, the suture strand having a tensioning free end and an opposite tissue-fixation end, a tissue-fixation device, such as a mesh disk or button, coupled to the tissue-fixation end of the suture strand, and a locking structure, such as barbs, disposed on the suture strand; passing the pre-loaded soft anchor through tissue; installing the pre-loaded soft anchor in a hole formed in bone; and pulling the tensioning free end of the suture strand to draw the disk against the tissue to approximate the tissue to bone and draw at least a portion of the barbs into the tubular sheath of the soft anchor thereby locking the suture construct in place.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawing figures.

DETAILED DESCRIPTION OF THE PREFERRED EMBODIMENTS

Figure 1:
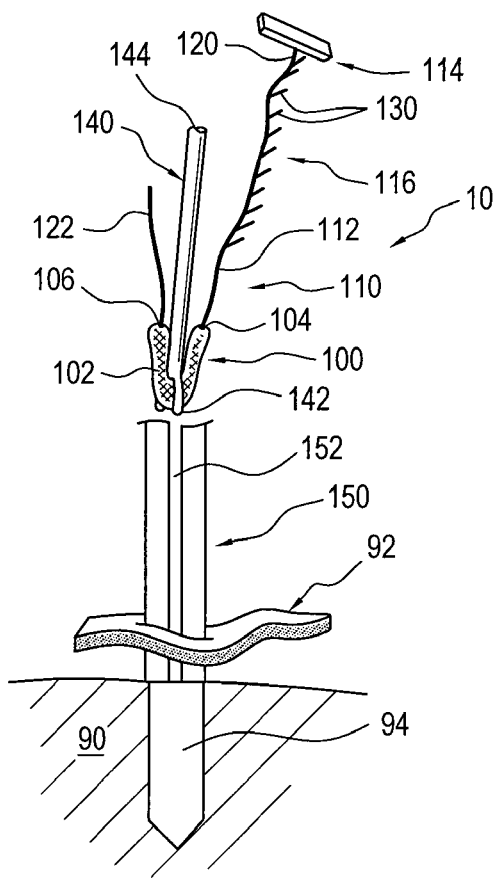
FIG. 1 is a schematic elevational view of a suture anchor assembly according to an exemplary embodiment of the present invention, showing the suture anchor assembly being inserted via an inserter into a guide located over a bone hole in accordance with a method of tissue repair of the present invention.

Referring to FIGS. 1-4, a suture anchor assembly 10 for tissue fixation is provided in accordance with an exemplary embodiment of the present. The suture anchor assembly 10 of the present invention provides for a simplified tissue repair while also ensuring positive fixation of the tissue to bone.

Suture anchor assembly 10 generally includes a soft suture anchor 100 and a suture construct 110 coupled thereto. Soft suture anchor 100 may include a tubular sheath 102, such as disclosed in commonly assigned U.S. Pat. No. 9,463,011 to Dreyfuss et al., the subject matter of which is herein incorporated by reference, made of flexible material, such as polyester or the like. Tubular sheath 102 may be a woven, braided, or knitted structure, and/or may be formed of yarns, fibers, filaments, sutures or similar materials, or combinations of these materials. Tubular sheath 102 has opposing open ends 104 and 106 through which suture construct 110 may extend.

Suture construct 110 may generally include a flexible suture strand 112, a tissue-fixation device 114, and a locking structure 116. Strand 112 has a tissue-fixation end 120 and an opposite tensioning free end 122. Tissue-fixation end 120 preferably extends through opening 104 of tubular sheath 102 and tensioning free end 122 preferably extends through opening 106. Tissue-fixation end 120 and tensioning free end 122 of strand 112 may also extend through respective openings in the length of tubular sheath 102 near or spaced from ends 104 and 106, as disclosed in U.S. Pat. No. 9,463,001 to Dreyfuss et al. Tensioning free end 122 may include a loop or eyelet 124 (FIG. 3) to assist in pulling suture strand 112.

Figure 4:
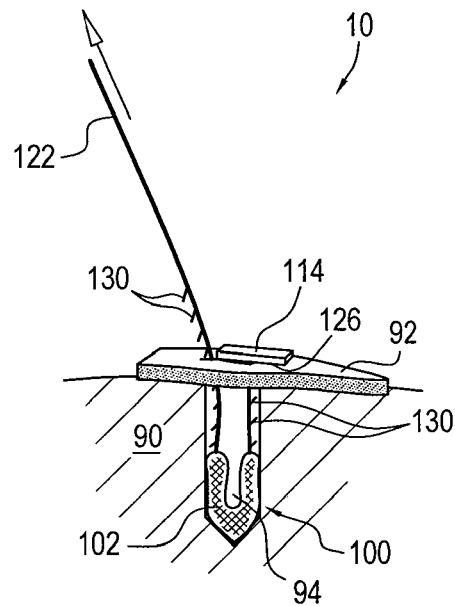
FIG. 4 is a schematic elevational view similar to FIG. 3 showing the tissue fixed to bone and the suture anchor assembly locked in place after the step of FIG. 2 in accordance with the method of tissue repair.

Tissue-fixation device 114 is preferably coupled to tissue-fixation end 120 of strand 112 by any known attachment, such as tying or adhering the strand 112 to device 114. Tissue fixation device 114 preferably has a disk or button shape and may be formed of any biocompatible material. Tissue-fixation device 114 may have other shapes, such as ring, straight or bended bar, cross and the like. Tissue-fixation device 114 may be generally solid, such as a polymer, or may be flexible, such as a mesh. Tissue-fixation device 114 includes a surface area 126 for abutting against tissue, as best seen in FIG. 4.

Locking structure 116 is provided on flexible strand 112 to prevent loosening of the suture construct 110 once tissue 92 is secured against the bone 90. Locking structure 116 is preferably configured to provide a one-way lock. The one-way lock of locking structure 116 may be created, for example, using one or more uni-directional barbs 130. As seen in the figures, these barbs 130 preferably angle outwardly in a direction toward tissue-fixation device 114. The one or more barbs 130 may be provided on a portion of suture strand 112, preferably a portion of suture strand 112 that is closer to the tissue-fixation end 120 than the tensioning free end 122. Alternatively, barbs 130 may be provided continuously or discontinuously along the length of suture strand 112. And the barbs 130 may extend from one or more sides or areas of suture strand 112. In a preferred embodiment, the barbs 130 are overmolded onto suture strand 112.

Figure 2:
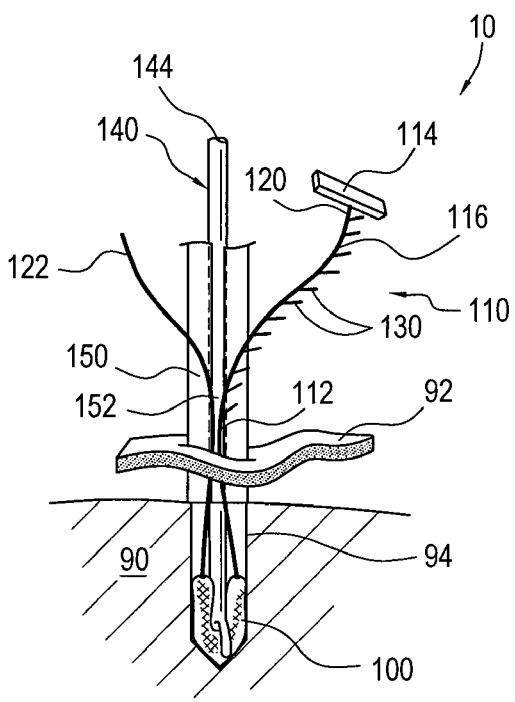
FIG. 2 is a schematic elevational view similar to FIG. 1 showing a soft anchor of the suture anchor assembly and an end of the inserter received in the bone hole after the step of FIG. 1, in accordance with the method of tissue repair.

A method of tissue repair using the suture anchor assembly 10 of the present invention generally includes the steps of passing suture anchor assembly 10 through the tissue 92, as seen in FIGS. 1 and 2, then installing soft anchor 100 of assembly 10 into a hole/socket of the bone 90, as seen in FIG. 2, and finally pulling suture strand 112 to draw tissue-fixation device 114 against the tissue 92 to secure the tissue 92 against the bone 90.

More specifically, the method may include the initial step of loading soft anchor 100 with suture construct 110 by passing tensioning free end 122 of suture strand 112 through tubular sheath 102 such that tissue-fixation end 120 of strand 112 extends through sheath opening 104 and tensioning free end 122 extends through sheath opening 106. Alternatively, tissue-fixation end 120 and tensioning free end 122 may extend through respective openings in the length of tubular sheath 102 near or spaced from ends 104 and 106.

Soft anchor 100 pre-loaded with suture construct 110 is passed through the tissue 92 and installed into a pre-drilled hole/socket 94 of the bone 90. For optimal installation of suture construct assembly 10, an inserter 140 and a guide 150 are preferably used, as best seen in FIGS. 1 and 2. Inserter 140 includes an end 142, such as a forked tip, that is designed to capture soft anchor 100. Once the end 142 of inserter 140 captures soft anchor 100, soft anchor 100 along with suture construct 110 may be pushed through guide 150 which has been inserted through the tissue 90 and positioned over the pre-drilled hole 94 in the bone 90, as seen in FIG. 1. This facilitates installation of soft anchor 100 into the bone hole 94. To assist with the advancement and installation of soft anchor 100 into the bone hole 94, an impact or mallet tool may be applied to the opposite end 144 of inserter 140. Insertion of soft anchor 100 into bone hole 94, as seen in FIG. 2 preferably forms a tight fit to anchor soft anchor 100 therein. When received in the bone hole 94, tubular sheath 102 preferably bunches up within the bone hole 94 in a similar manner as disclosed in U.S. Pat. No. 9,463,001 to Dreyfuss et al. That is, soft anchor 100 may be inserted in a doubled over manner so that the ends of tubular sheath 102 are following its middle portion once set in bone, such that when tension is pulled on the suture construct 110, the soft anchor 100 bunches up to take up more room in bone hole 94 and therefore fixes in place. Also, the material of tubular sheath 102, such as a braid, may assist with anchoring of soft anchor 100 because of its loose composition together with the trabecular cancellous nature of the bone creates a fixation therebetween.

Figure 3:
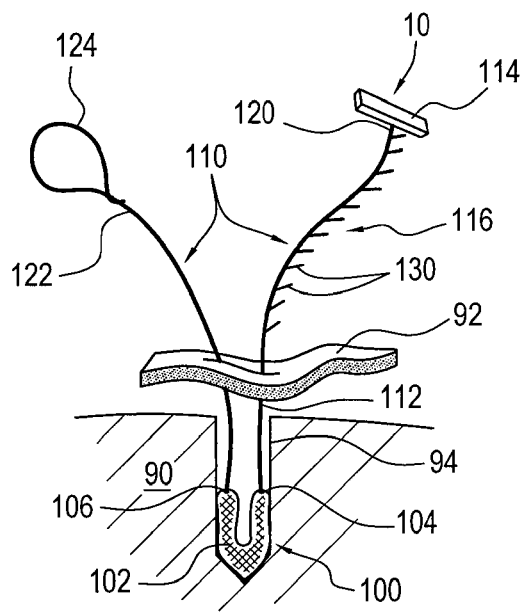
FIG. 3 is a schematic elevational view similar to FIG. 2 showing the inserter and guide removed after the step of FIG. 2 in accordance with the method of tissue repair.

Once soft anchor 100 is installed in bone hole 94, inserter 140 and guide 150 may be removed. In a preferred embodiment, guide 150 includes an elongated slot 152 along its length, as best in FIG. 1, which allows suture strand 112 to escape and thus not interfere with the guide's removal. As seen in FIG. 3, once soft anchor 100 is installed in bone hole 94, tissue-fixation end 120 of strand 112 with tissue fixation device 114 and tensioning free end 122 remain outside of bone hole 94. That is, when soft anchor 100 preloaded with suture construct 110 is passed through the tissue 92, the tissue-fixation and tensioning free ends 120 and 122 remain and are not passed through the tissue 92.

As seen in FIG. 4, tensioning free end 122 of suture strand 112 may then be pulled away from the bone 90 in a tightening direction to pull strand 112 through tubular sheath 102 of soft anchor 100 and draw tissue-fixation device against the tissue 92. The uni-directional nature of barbs 130 allows the suture strand 112 and locking structure 116 to be pulled, via tensioning free end 122, unobstructed in one direction, that is, in the tightening direction, through the tissue 92 and tubular sheath 102, while preventing the strand 112 from moving in the opposite direction, that is, in the loosening direction. Tissue-fixation device 114, and particularly its surface area 126, applies a compressive force to the tissue 92 as strand 112 is being pulled to approximate the tissue 92 to bone 90. Barbs 130 engage tubular sheath 102 to lock suture construct 110 in place to secure the attachment of the tissue 92 to the bone 90. The uni-directional nature and angle of barbs 130 prevents tissue-fixation device 114 or strand 112 from loosening.

While particular embodiments have been chosen to illustrate the invention, it will be understood by those skilled in the art that various changes and modifications can be made therein without departing from the scope of the invention as defined in the appended claims.

What is claimed is:

1. A method of tissue repair, comprising the steps of:
   loading a soft anchor with a suture construct including a suture strand passing through a tubular sheath of the soft anchor, the suture strand having a tensioning free end and an opposite tissue-fixation end, a tissue-fixation device coupled to the tissue-fixation end of the suture strand, and a locking structure disposed on the suture strand;
   passing the pre-loaded soft anchor through tissue;
   installing the pre-loaded soft anchor in a hole formed in bone; and
   pulling the tensioning free end of the suture strand to draw the tissue-fixation device against the tissue to approximate the tissue to bone and draw at least a portion of the locking structure into the tubular sheath of the soft anchor, thereby locking the suture construct in place.

2. A method according to claim 1, wherein, when the soft anchor is passed through the tissue, the tensioning free end and the tissue-fixation end of the suture strand remain and are not passed through the tissue.

3. A method according to claim 1, wherein pulling the tensioning free end of the suture strand pulls the locking structure through the tissue.

4. A method according to claim 3, wherein the locking structure includes barbs that angle outwardly in a direction toward the tissue-fixation device to facilitate passage of the locking structure through the tissue and facilitate a one-way locking engagement with the tubular sheath of the soft anchor.

5. A method according to claim 1, wherein the step of passing the pre-loaded soft anchor through tissue includes passing the pre-loaded soft anchor through a guide that was previously passed through the tissue.

6. A method according to claim 5, further comprising the step of removing the guide once the soft anchor is installed in the hole formed in bone.

7. A method according to claim 6, wherein the guide includes an elongated slot to facilitate removal of the guide without interfering with the suture construct.

8. A method according to claim 1, wherein the soft anchor is installed into the hole formed in bone by capturing the tubular sheath of the soft anchor with an inserter and malleting the inserter to advance the soft anchor into the hole.

9. A method according to claim 1, further comprising the step of overmolding the locking structure on the tissue-fixation end of the suture strand.

10. A method according to claim 1, wherein the suture strand is passed through open ends of the tubular sheath.

11. A method according to claim 1, wherein the step of pulling the tensioning free end includes pulling a loop on the tensioning free end of the suture strand.

\* \* \* \* \*